United States Patent
Sakai et al.

(10) Patent No.: US 10,219,342 B2
(45) Date of Patent: Feb. 26, 2019

(54) LIGHT SOURCE DEVICE AND CONTROL METHOD OF LIGHT SOURCE DEVICE

(71) Applicant: OLYMPUS CORPORATION, Hachioji-shi, Tokyo (JP)

(72) Inventors: Aiko Sakai, Kodaira (JP); Yusuke Yabe, Chofu (JP); Tomoya Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/383,131

(22) Filed: Dec. 19, 2016

(65) Prior Publication Data

US 2017/0105258 A1 Apr. 13, 2017

Related U.S. Application Data

(63) Continuation of application No. PCT/JP2015/077934, filed on Oct. 1, 2015.

(30) Foreign Application Priority Data

Oct. 10, 2014 (JP) .................................. 2014-209000

(51) Int. Cl.
*H05B 33/08* (2006.01)
*A61B 1/04* (2006.01)
(Continued)

(52) U.S. Cl.
CPC ........... *H05B 33/0848* (2013.01); *A61B 1/04* (2013.01); *A61B 1/0661* (2013.01);
(Continued)

(58) Field of Classification Search
CPC ............ H05B 33/0869; H05B 33/0851; H05B 33/086; H05B 33/0845; H05B 41/325;
(Continued)

(56) References Cited

U.S. PATENT DOCUMENTS 6,400,099 B1 * 6/2002 Walker ..................... B41J 2/125
250/552
8,785,833 B2 7/2014 Yabe et al.
(Continued)

FOREIGN PATENT DOCUMENTS

CN 101940062 A 1/2011
JP 2012-019983 A 2/2012
(Continued)

OTHER PUBLICATIONS

May 31, 2016 Office Action issued in Japanese Patent Application No. 2016-507709.
(Continued)

*Primary Examiner* — Douglas W Owens
*Assistant Examiner* — Pedro C Fernandez
(74) *Attorney, Agent, or Firm* — Oliff PLC

(57) ABSTRACT

A light source device includes a semiconductor light source, a light source control section, an optical sensor, a sensor control section, and an intensity adjusting section. The light source control section controls a light quantity per field of light to be emitted from the semiconductor light source, by pulse width modulation. The optical sensor receives the light emitted from the semiconductor light source to acquire a quantity of the received light. The sensor control section controls the optical sensor to detect the light in an exposure period shorter than a minimum pulse width in the pulse width modulation, thereby acquiring the quantity of the received light which is acquired by the optical sensor. The intensity adjusting section adjusts emission intensity of the semiconductor light source on the basis of the quantity of the received light.

16 Claims, 4 Drawing Sheets

(51) Int. Cl.
  *G02B 23/24* (2006.01)
  *A61B 1/06* (2006.01)
(52) U.S. Cl.
  CPC ..... *G02B 23/2461* (2013.01); *H05B 33/0869* (2013.01); *A61B 1/06* (2013.01)
(58) Field of Classification Search
  CPC ................ H05B 41/3922; H05B 37/02; H05B 33/0848; Y02B 20/46; A61B 1/04; A61B 1/0661; G02B 23/2461
  USPC ....... 315/151, 158, 159, 307, 152, 291, 297; 250/205; 396/159
  See application file for complete search history.

(56) References Cited

U.S. PATENT DOCUMENTS

| | | | | |
|---|---|---|---|---|
| 2011/0309754 | A1* | 12/2011 | Ashdown | H05B 33/0818 315/151 |
| 2012/0016201 | A1 | 1/2012 | Seto et al. | |
| 2014/0104403 | A1 | 4/2014 | Ogasawara | |
| 2014/0340572 | A1* | 11/2014 | Sato | G03B 7/08 348/370 |

FOREIGN PATENT DOCUMENTS

| | | |
|---|---|---|
| JP | 2012-21889 A | 2/2012 |
| JP | 2013-215435 A | 10/2013 |
| JP | 5379932 B1 | 12/2013 |
| JP | 5467182 B1 | 4/2014 |
| WO | 2013/094457 A1 | 6/2013 |
| WO | 2013/150897 A1 | 10/2013 |

OTHER PUBLICATIONS

Dec. 15, 2015 International Search Report issued in Patent Application No. PCT/JP2015/077934.
Apr. 20, 2017 Notification of Transmittal of Translation of IPRP issued in International Application No. PCT/JP2015/077934.
Jul. 3, 2018 Extended Search Report issued in European Patent Application No. 15848793.4.
Feb. 24, 2018 Office Action issued in Chinese Patent Application No. 201580030534.1.
Aug. 14, 2018 Office Action issued in Chinese Patent Application No. 201580030534.1.

* cited by examiner

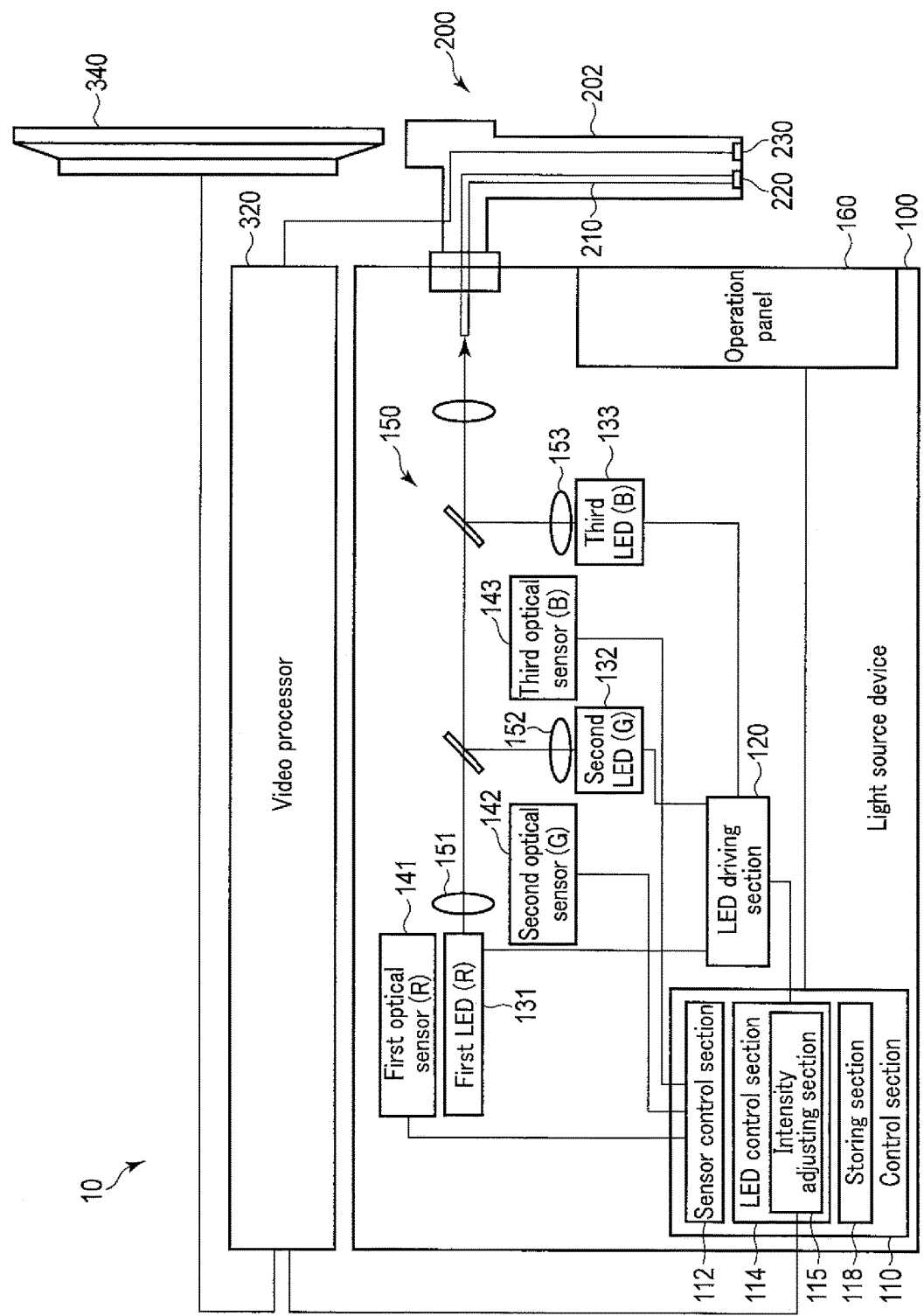
F I G. 1

LIGHT SOURCE DEVICE AND CONTROL METHOD OF LIGHT SOURCE DEVICE

CROSS-REFERENCE TO RELATED APPLICATIONS

This application is a Continuation application of PCT Application No. PCT/JP2015/077934, filed Oct. 1, 2015 and based upon and claiming the benefit of priority from prior Japanese Patent Application No. 2014-209000, filed Oct. 10, 2014, the entire contents of all of which are incorporated herein by reference.

BACKGROUND OF THE INVENTION

1. Field of the Invention

The present invention relates to a light source device and a control method of the light source device.

2. Description of the Related Art

A light source device for illumination device of an endoscope is disclosed in, for example, International Publication No. 2013/150897. In this light source device, a red LED, a green LED and a blue LED are used as light sources. This light source device combines the light emitted from these LEDs to emit white light as illumination light. The light source device is provided with an optical sensor that detects a quantity of the light emitted from each LED. On the basis of the light quantity detected by the optical sensor, the light source device adjusts emission intensity of each LED and regulates a color of the illumination light into appropriate white. However, in International Publication No. 2013/150897, it is not specifically disclosed how to detect the light quantity of each LED.

For example, in an endoscope system, there is a width of several thousand times between a maximum light quantity and a minimum light quantity of the illumination light. Furthermore, for example, for the purpose of adjusting a color balance, it is necessary to adjust the light quantity of each color at a level of several %. Consequently, as a detection range of the optical sensor, there is required a wide range in which a maximum value is tens of thousands times as large as a minimum value. However, a usual optical sensor does not have such a wide detection range.

BRIEF SUMMARY OF THE INVENTION

According to an aspect of the present invention, a light source device includes a semiconductor light source; a light source control section that controls a light quantity per field of light to be emitted from the semiconductor light source, by pulse width modulation; an optical sensor that receives the light emitted from the semiconductor light source to acquire a quantity of the received light; a sensor control section that controls the optical sensor to detect the light in an exposure period shorter than a minimum pulse width in the pulse width modulation, thereby acquiring the quantity of the received light which is acquired by the optical sensor; and an intensity adjusting section that adjusts emission intensity of the semiconductor light source on the basis of the quantity of the received light.

According to an aspect of the present invention, a control method of a light source device includes controlling a light quantity per field of light to be emitted from a semiconductor light source, by pulse width modulation; controlling an optical sensor to detect the light emitted from the semiconductor light source in an exposure period shorter than a minimum pulse width in the pulse width modulation, thereby acquiring a quantity of the received light from the optical sensor; and adjusting emission intensity of the semiconductor light source on the basis of the quantity of the received light.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing an outline of a configuration example of an endoscope system according to one embodiment of the present invention;

DETAILED DESCRIPTION OF THE INVENTION

Figure 2:
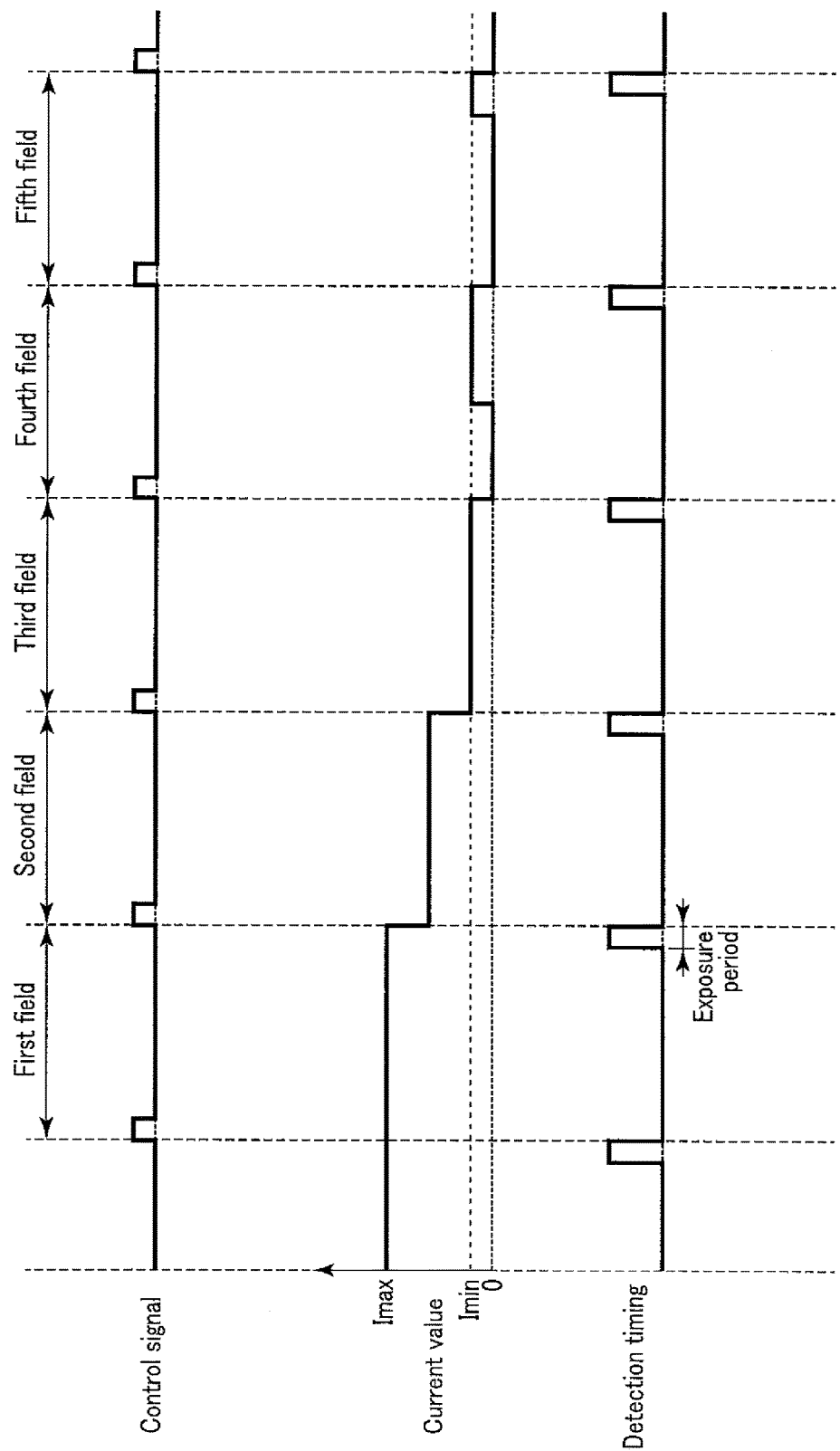
FIG. 2 is a timing chart showing one example of an operation of a light source device according to the one embodiment.

One embodiment of the present invention will be described with reference to the drawings. As shown in FIG. 1, an endoscope system 10 according to the present embodiment comprises a light source device 100 to emit illumination light, an endoscope 200, a video processor 320, and a monitor 340.

The endoscope 200 is a usual endoscope including an inserting portion 202 having an elongated shape. The endoscope 200 comprises a light guide 210, a lens 220, and an image sensor 230. The light guide 210 guides the light emitted from the light source device 100 along the inserting portion 202 of the endoscope 200 to a distal end of the inserting portion 202. The lens 220 is disposed at the distal end of the inserting portion 202. The lens 220 emits the light guided by the light guide 210 as the illumination light. The image sensor 230 is disposed in the distal end of the inserting portion 202. The image sensor 230 is an element such as a CCD image sensor or a CMOS image sensor. The image sensor 230 images a region illuminated with the light emitted from the lens 220, and generates an image signal.

The light source device 100 is a device that functions as a light source of the illumination light of the endoscope 200. In the present embodiment, a light emitting diode (LED) is used as the light source. The light source is not limited to the LED and may be a laser diode or the like, and various semiconductor light sources are usable. The light source device 100 comprises a control section 110 and an LED driving section 120.

The light source device 100 comprises, as the light sources thereof, a first LED 131 that emits red light (R), a second LED 132 that emits green light (G), and a third LED 133 that emits blue light (B). Furthermore, the light source device 100 comprises an optical system 150. The optical system 150 includes a first collimating lens 151 that forms light emitted from the first LED 131 into parallel light, a second collimating lens 152 that forms light emitted from the second LED 132 into parallel light, and a third collimating lens 153 that forms light emitted from the third LED 133 into parallel light. Furthermore, the optical system 150 includes a dichroic filter, a mirror and the like which combine the light emitted from the condensing lenses to guide the light to a light guide connector. In this way, the light source device 100 includes the light sources in which wavelengths are different from one another. Hereinafter, the first LED 131, the second LED 132 and the third LED 133 will collectively and simply be referred to as the LEDs as required.

The light source device 100 comprises a first optical sensor 141 that detects intensity of the red light emitted from the first LED 131, a second optical sensor 142 that detects intensity of the green light emitted from the second LED 132, and a third optical sensor 143 that detects intensity of the blue light emitted from the third LED 133. In this way, the light source device 100 includes the sensors each of which acquires a quantity of received light for each wavelength. Hereinafter, the first optical sensor 141, the second optical sensor 142 and the third optical sensor 143 will collectively be referred to as the optical sensors as required.

The LED driving section 120 drives each of the first LED 131, the second LED 132 and the third LED 133.

The control section 110 includes a circuit such as a central processing unit (CPU) or an application specific integrated circuit (ASIC). The control section 110 operates in accordance with a program stored in an after-mentioned storing section 118. The control section 110 has a sensor control section 112, an LED control section 114, and the storing section 118.

The sensor control section 112 controls an operation of each optical sensor. The sensor control section 112 acquires a value concerned with the light quantity detected by each of the first optical sensor 141, the second optical sensor 142 and the third optical sensor 143.

The LED control section 114 controls an operation of each LED to be driven by the LED driving section 120. That is, the LED control section 114 controls a current to be supplied to each LED, thereby adjusting emission intensity of each LED. The LED control section 114 has an intensity adjusting section 115. The intensity adjusting section 115 adjusts the current to be supplied to each LED on the basis of values detected by the optical sensors which are acquired by the sensor control section 112. The intensity adjusting section 115 adjusts the current to be supplied to each LED to adjust, for example, a color balance.

The storing section 118 can include a usual memory. The storing section 118 stores various programs, and information such as an after-mentioned relation between a current flowing through the LEDs and the emission intensity of the LEDs.

Under the control of the LED control section 114, the light emitted from the first LED 131, the second LED 132 and the third LED 133 is combined by the optical system 150. The combined light becomes white light. The combined white light is introduced into the light guide 210. As described above, the light is guided to the distal end of the inserting portion 202 of the endoscope 200 and emitted as the illumination light. It is necessary to appropriately adjust the light quantity of each color light to be emitted from each LED so that the combined light becomes the appropriate white light.

The first optical sensor 141 is disposed at, for example, a position to receive a part of light which is emitted from the first LED 131 and does not enter the first collimating lens 151 due to the wide distribution. Similarly, the second optical sensor 142 is disposed at, for example, a position to receive a part of light which is emitted from the second LED 132 and does not enter the second collimating lens 152 due to the wide distribution. The third optical sensor 143 is disposed at, for example, a position to receive a part of light which is emitted from the third LED 133 and does not enter the third collimating lens 153 due to the wide distribution. Each of the first optical sensor 141, the second optical sensor 142 and the third optical sensor 143 operates under the control of the sensor control section 112 and detects the light of each wavelength. The optical sensor transmits the detected light quantity to the sensor control section 112.

An operation panel 160 functions as an operating section which accepts a user's operation. The operation panel 160 includes, for example, a switch, a dial, a keyboard, a touch panel or the like.

The video processor 320 acquires the image signal obtained by the image sensor 230 disposed in the endoscope 200. The video processor 320 subjects the acquired image signal to image processing. The video processor 320 outputs a display signal to the monitor 340 to display an image obtained by the image sensor 230 in the monitor 340. Furthermore, the video processor 320 calculates a ratio between an average luminance of the image generated by an imaging signal output from the endoscope 200 and a predetermined target luminance, and outputs brightness control information indicating the calculated ratio to the control section 110 of the light source device 100.

The monitor 340 is a usual monitor such as a liquid crystal display or a CRT display. The monitor 340 displays the image obtained by the endoscope 200 on the basis of the display signal prepared by the video processor 320.

An operation of the endoscope system 10 according to the present embodiment will be described. First, control of the light quantity and detection of the light quantity in the light source device 100 will be described with reference to a timing chart shown in FIG. 2. The light quantity of the light to be emitted from the LEDs that are the light source of the light source device 100 according to the present embodiment is controlled by a combination of a value of the current flowing through the LED and time for which the current flows in every predetermined field. It is to be noted that a length of each field is arbitrary, but is, for example, 16.67 ms (60 Hz).

An upper panel of FIG. 2 shows a control signal. The control signal is a periodic pulse signal. This pulse signal adjusts a timing of start of the field. A middle panel of FIG. 2 shows a value of the current to be supplied to the LED. The current to be supplied to the LED can be adjusted in stages between a maximum current Imax and a minimum current Imin. A lower panel of FIG. 2 shows a timing at which the optical sensors detect the light quantity.

As shown in the middle panel of FIG. 2, when the quantity of the light to be emitted is high, the value of the current flowing through the LED in each field is controlled, thereby adjusting the quantity of the light to be emitted from the LED. At this time, the current is supplied to the LED over the whole period in the field. The value of the current is adjusted in stages from the maximum current Imax to the minimum current Imin. For example, in FIG. 2, in the first field, the value of the current indicates the maximum current Imax, and the light quantity is maximum. In a second field, the quantity of the light to be emitted is lower than that in the first field, and in a third field, the quantity of the light to be emitted further decreases. In this way, the quantity of the light to be emitted per unit time is adjusted in accordance with the emission intensity of the LED.

In a case of emitting the light of the light quantity lower than that when the current value indicates the minimum current Imin, a period to apply the minimum current Imin is adjusted. That is, the light quantity of the LED is controlled by pulse width modulation (PWM). At this time, the current flowing through the LED is constant at the minimum current Imin. In each field, the period in which the current flows through the LED is present toward an end side of each field. That is, in the respective fields, a timing to start the supply of the current varies, and a timing to end the supply of the current is a timing of end of each field.

For example, in FIG. 2, a pulse width in a fourth field is narrower than that in the third field, and the light quantity per field of the light to be emitted in the fourth field is lower than that in the third field. Similarly, a pulse width in a fifth field is narrower than that in the fourth field, and the light quantity per field of the light to be emitted in the fifth field is lower than that in the fourth field. In this way, when the light quantity of the light to be emitted is low, the emission intensity of the LED is constant, but when an emission period varies, the light quantity per unit time of the light to be emitted is adjusted.

As described above, a combination of the control of the current value and PWM control can achieve a wide dynamic range in the LED that is the light source of the light source device 100. For example, when the maximum current Imax is five times as large as the minimum current Imin and a minimum pulse width is 1/1000 of one field, a ratio between a maximum value and a minimum value of the quantity of the light to be emitted by the LED is 5000:1.

As shown in the lower panel of FIG. 2, a period in which the optical sensor detects the light quantity, i.e., an exposure period of the optical sensor is set to a predetermined period just before the end of each field. This exposure period is shorter than a period corresponding to the minimum pulse width in the PWM control of the LED. In this way, the optical sensor can acquire the value concerned with the emission intensity of the LED per unit time to the value of the current to be supplied to the LED irrespective of the pulse width.

The control section 110 sets a light quantity control pattern for adjustment of the light quantity of the green light to be emitted from the second LED 132 that is a reference LED (a drive current value of the second LED 132 and a set value of the pulse width during PWM drive) on the basis of a light quantity command value and timing information output from the video processor 320. Furthermore, the control section 110 is configured to control the LED driving section 120 in every filed to drive the second LED 132 that emits the green light in the light quantity corresponding to the brightness control information, on the basis of the brightness control information output from the video processor 320, and the light quantity control pattern.

The control section 110 adjusts the light quantity of the red light to be emitted from the first LED 131 that is different from the reference LED, by use of a control pattern similar to the light quantity control pattern applied to the second LED 132 that emits the green light. Furthermore, on the basis of a light quantity detection signal output in the exposure period of the first optical sensor 141, a light quantity detection signal output in the exposure period of the second optical sensor 142, and the light quantity control pattern, the control section 110 calculates a light quantity ratio to obtain a predetermined color balance or the color balance set in accordance with an operation of the operation panel 160, as a light quantity ratio of the red light in a case where the light quantity of the green light is a reference light quantity. For the purpose of driving the first LED 131 that emits the red light in the light quantity corresponding to the calculated light quantity ratio, in every field, the control section 110 adjusts the pulse width of the PWM drive when driving the first LED 131 so that the pulse width is common with the pulse width when driving the second LED 132, whereas the control section 110 controls the LED driving section 120 to adjust the drive current value into a current value based on the above light quantity ratio.

The control section 110 adjusts the light quantity of the blue light to be emitted from the third LED 133 that is different from the reference LED by use of a control pattern similar to the light quantity control pattern applied to the second LED 132 that emits the green light. Furthermore, on the basis of a light quantity detection signal output in the exposure period of the second optical sensor 142, a light quantity detection signal output in the exposure period of the third optical sensor 143, and the light quantity control pattern, the control section 110 calculates a light quantity ratio to obtain the predetermined color balance or the color balance set in accordance with the operation of the operation panel 160, as a light quantity ratio of the blue light in the case where the light quantity of the green light is the reference light quantity. For the purpose of driving the third LED 133 that emits the blue light in the light quantity corresponding to the calculated light quantity ratio, in every field, the control section 110 adjusts the pulse width of the PWM drive when driving the third LED 133 so that the pulse width is common with the pulse width when driving the second LED 132, whereas the control section 110 controls the LED driving section 120 to adjust the drive current value into the current value based on the above light quantity ratio.

That is, the control section 110 has a function of a color balance adjusting section, and on the basis of light quantity detection signals output in exposure periods of the first optical sensor 141, the second optical sensor 142 and the third optical sensor 143, and the light quantity control pattern, the control section 110 executes control to drive the first LED 131 and the third LED 133, thereby adjusting a color balance of the red light, the green light and the blue light.

According to the present embodiment, the emission intensity of the LED which is changeable in accordance with situations can correctly be detected with one sensor. That is, as described above, minimum emission quantity of the LED is, for example, 1/5000 of maximum emission quantity. For the purpose of correctly acquiring the emission quantity to adjust the emission quantity, there is required a sensitivity to detect a difference of about 1/100 of 1/5000. That is, for example, when the optical sensor detects the light quantity per field of the light emitted from the LED, the optical sensor requires a dynamic range of, for example, about 1:500000. In general, it is difficult to achieve such a wide dynamic range with one optical sensor. To eliminate such a problem, for example, optical sensors which are different in detection level range are combined and used, so that the wide dynamic range can be achieved. However, when a plurality of the optical sensors is used, cost of the light source device increases.

On the other hand, in the present embodiment, the optical sensor detects the emission intensity of the LED in the exposure period shorter than the minimum pulse width of the emission of the LED. Therefore, in the above-mentioned example, the minimum emission intensity of the LED in this exposure period is, for example, ⅕ of the maximum emission intensity. Therefore, the optical sensor may have a dynamic range of about 1:500. In this way, according to the present embodiment, it is possible to accurately detect the required emission intensity at low cost.

According to the present embodiment, it is possible to correctly detect the emission intensity of each of the LEDs which are different in emission color, and hence it is possible to accurately adjust the emission quantity of each LED. Consequently, it is possible to accurately achieve modulation of the light such desired color adjustment.

Figure 3:
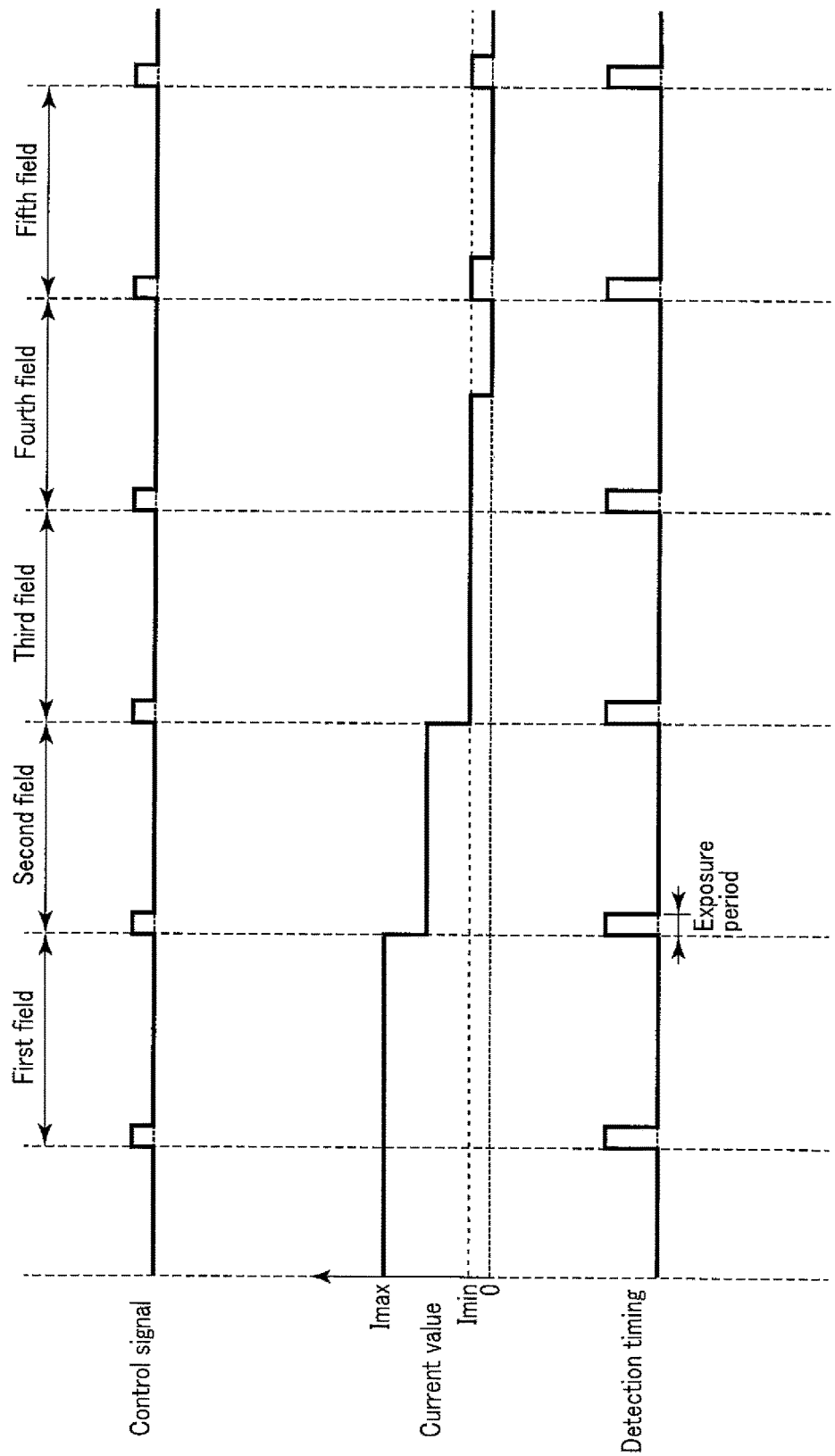
FIG. 3 is a timing chart showing one example of an operation of a light source device according to a modification.

It is to be noted that in the above-mentioned embodiment, as shown in FIG. 2, the emission period is adjusted on the basis of the end of each field in the PWM control of the emission of the LED, but the present invention is not limited to this embodiment. As shown in FIG. 3, the emission period may be adjusted on the basis of the start of each field. In this case, the exposure period is the period that starts with the start of each field.

Figure 4:
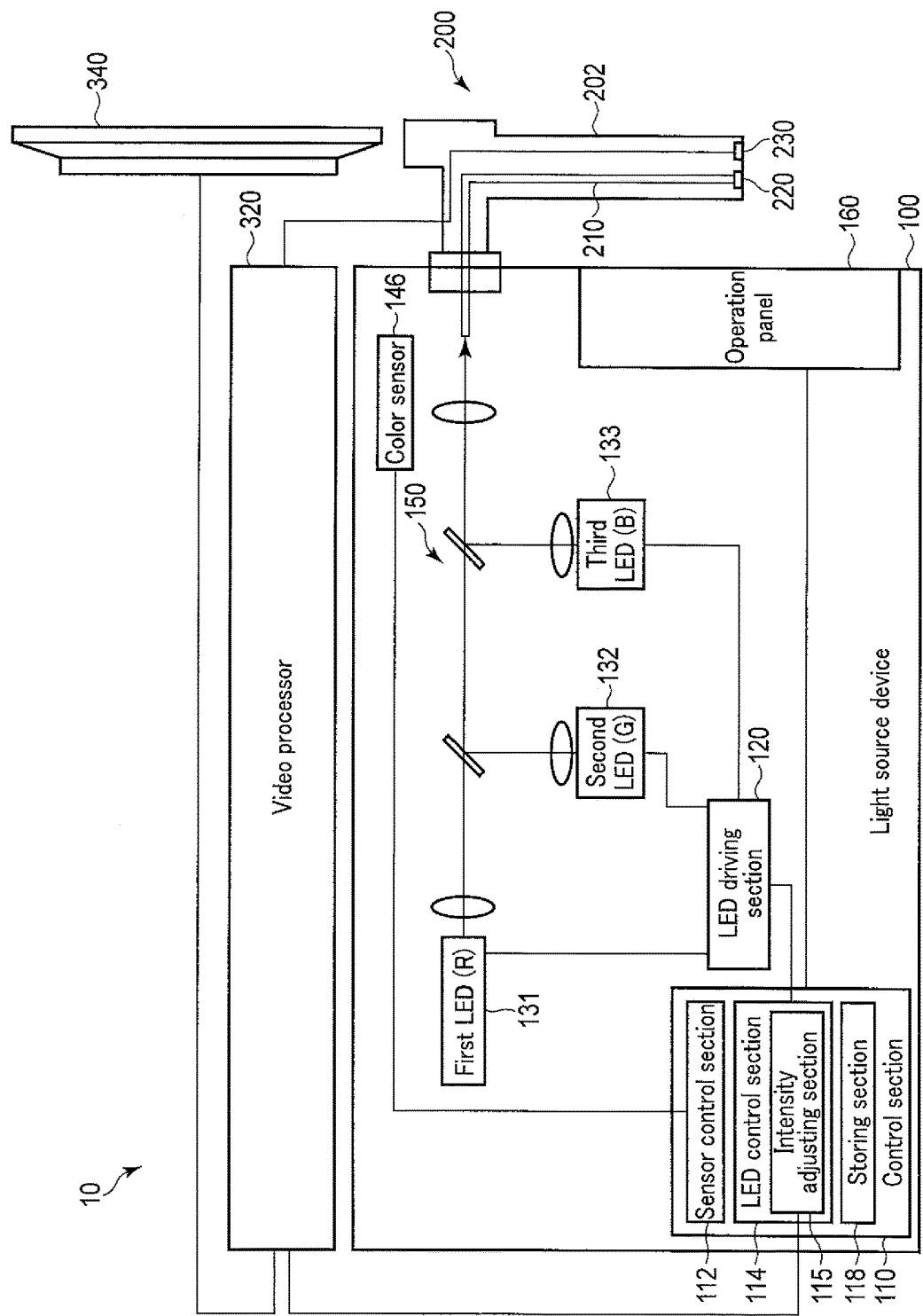
FIG. 4 is a block diagram showing an outline of a configuration example of an endoscope system according to a modification.

Furthermore, in the above-mentioned embodiment, there has been described an example where three optical sensors are disposed to correspond to three LEDs, but the present invention is not limited to this embodiment. For example, white light obtained by combining light emitted from three LEDs may be split and detected. In this case, for example, as shown in FIG. 4, a color sensor 146 is disposed in place of the first optical sensor 141, the second optical sensor 142 and the third optical sensor 143. The color sensor 146 is disposed at a position to detect leakage light in, for example, a portion in which combined illumination light enters a light guide 210. The color sensor 146 has a spectroscopic function, and is constituted to detect a light quantity of each wavelength and transmit a value of the light quantity to a sensor control section 112.

In the above-mentioned embodiment, there has been described an example where three light sources which are different in wavelength of light to be emitted are disposed and a light quantity of the light to be emitted from each light source is adjusted, but the present invention is not limited to this embodiment. For example, the present embodiment is also applicable to a case where a light source is one light source that emits white light and a light quantity of the light to be emitted from this light source is adjusted. Furthermore, this also applies to a case where the number of the light sources is four or more. In this way, the number of the light sources may be any number.

Furthermore, in the above embodiment, there has been described an example where three kinds of light in different colors are combined to become white light, but the present invention is not limited to this embodiment. For example, the above-mentioned embodiment is similarly applicable also to a constitution in which an image sensor does not have a spectroscopic function, three kinds of light in different colors are emitted in order, and images of a subject illuminated with the three kinds of light in different colors are successively photographed, thereby acquiring a color image in a time division manner.

There might be a case where it is necessary to emit light in a remarkably low light quantity and a pulse width of the light to be emitted from the LED has to be set to be smaller than an exposure period of the optical sensor. In this case, there is the possibility that an adjustment value based on a detection value of the optical sensor cannot be determined. In such a case, a previously determined adjustment value may be used as the adjustment value to be determined. In a case of a low light quantity, as compared with a high light quantity, a heating quantity is lower, and hence a difference from a reference value of emission intensity of the LED is small. Consequently, it is not necessary to determine the adjustment value with high accuracy, and even when the previously determined adjustment value is used, any problems might not occur.

A technology of the above-mentioned embodiment is not limited to the light source of the endoscope, and is applicable to various light source devices in which a light quantity per field of light to be emitted from a semiconductor light source is controlled by pulse width modulation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
a semiconductor light source;
a light source control section that controls a light quantity per cycle period of light to be emitted from the semiconductor light source, by controlling a current supplied to the semiconductor light source through: (A) adjusting a current value for the semiconductor light source over a whole cycle period in response to the light quantity per cycle period being higher than or equal to a predetermined value, and (B) adjusting a period of supplying a minimum current to the semiconductor light source by pulse width modulation in response to the light quantity per cycle being lower than the predetermined value;
an optical sensor that receives the light emitted from the semiconductor light source to acquire a quantity of the received light;
a sensor control section that controls the optical sensor to detect the light in an exposure period shorter than a minimum pulse width where the semiconductor light source is turned on by the pulse width modulation in any cycle period, thereby acquiring the quantity of the received light which is acquired by the optical sensor; and
an intensity adjusting section that adjusts emission intensity of the semiconductor light source on the basis of the quantity of the received light, wherein:
(i) the light source control section causes a light source driver to stop supplying current to the light source at the end of the cycle period, and the sensor control section causes the light sensor to stop measuring the received light at the end of the cycle period in any cycle period, or
(ii) the light source control section causes the light source driver to start supplying current to the light source at the start of the cycle period, and the sensor control section causes the light sensor to start measuring the received light at the start of the cycle period in any cycle period.

2. The light source device according to claim 1, wherein the light source control section controls the light quantity per cycle period on the basis of the pulse width modulation and the emission intensity of the semiconductor light source.

3. The light source device according to claim 1, wherein
the semiconductor light source includes light sources which are different in wavelength of the light to be emitted,
the optical sensor receives the light of each of the wavelengths,
the sensor control section acquires the quantity of the received light for each of the wavelengths, and
the intensity adjusting section adjusts the emission intensity of each of the light sources which are different in the wavelength, on the basis of the quantity of the received light for each of the wavelengths.

4. The light source device according to claim 3, wherein the optical sensor includes sensors for the respective wavelengths.

5. The light source device according to claim 3, wherein
the light emitted from each of the light sources is combined, and
the optical sensor splits the combined light to acquire the quantity of the received light for each of the wavelengths.

6. The light source device according to claim 3, wherein the intensity adjusting section adjusts the emission intensity of each of the light sources which are different in the wavelength to adjust a color balance.

7. The light source device according to claim 6, wherein the light sources include a first light source that emits red light, a second light source that emits green light, and a third light source that emits blue light.

8. The light source device according to claim 1, wherein a maximum current is five times as large as the minimum current and the minimum pulse width is 1/1000 of the cycle period.

9. A light source device comprising:
a semiconductor light source configured to emit light;
an optical sensor that receives the light emitted from the semiconductor light source;
at least one processor or integrated circuit programmed to:
control a light quantity per cycle period of the light emitted from the semiconductor light source by controlling a current supplied to the semiconductor light source through: (A) adjusting a current value for the semiconductor light source over a whole cycle period in response to the light quantity per cycle period being higher than or equal to a predetermined value, and (B) adjusting a period of supplying a minimum current to the semiconductor light source by pulse width modulation in response to the light quantity per cycle being lower than the predetermined value;
control the optical sensor to detect the emitted light in an exposure period shorter than a minimum pulse width where the semiconductor light source is turned on by the pulse width modulation in any cycle period, and determine a quantity of the received light acquired by the optical sensor; and
adjust emission intensity of the semiconductor light source based on of the determined quantity of the received light, wherein:
(i) the at least one processor or integrated circuit causes a light source driver to stop supplying current to the light source at the end of the cycle period, and causes the optical sensor to stop measuring the received light at the end of the cycle period in any cycle period, or
(ii) the at least one processor or integrated circuit causes the light source driver to start supplying current to the light source at the start of the cycle period, and causes the optical sensor to start measuring the received light at the start of the cycle period in any cycle period.

10. The light source device according to claim 9, wherein the at least one processor or integrated circuit is further programmed to:
control the light quantity per cycle period on the basis of the pulse width modulation and the emission intensity of the semiconductor light source.

11. The light source device according to claim 9, wherein
the semiconductor light source includes light sources which are different in wavelength of the light to be emitted,
the optical sensor receives the light of each of the wavelengths, and
the at least one processor or integrated circuit is further programmed to:
acquire the quantity of the received light for each of the wavelengths, and
adjust the emission intensity of each of the light sources which are different in the wavelength, on the basis of the quantity of the received light for each of the wavelengths.

12. The light source device according to claim 11, wherein the optical sensor includes sensors for the respective wavelengths.

13. The light source device according to claim 11, wherein
the light emitted from each of the light sources is combined, and
the optical sensor splits the combined light to acquire the quantity of the received light for each of the wavelengths.

14. The light source device according to claim 11, wherein the at least one processor or integrated circuit is further programmed to:
adjust the emission intensity of each of the light sources which are different in the wavelength to adjust a color balance.

15. The light source device according to claim 14, wherein the light sources include a first light source that emits red light, a second light source that emits green light, and a third light source that emits blue light.

16. The light source device according to claim 9, wherein a maximum current is five times as large as the minimum current and the minimum pulse width is 1/1000 of the cycle period.

* * * * *